(12) United States Patent
Lee et al.

(10) Patent No.: US 10,766,034 B2
(45) Date of Patent: Sep. 8, 2020

(54) OPTICAL CAVITY PCR

(71) Applicant: THE REGENTS OF THE UNIVERSITY OF CALIFORNIA, Oakland, CA (US)

(72) Inventors: Luke P. Lee, Orinda, CA (US); Jun Ho Son, Albany, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 307 days.

(21) Appl. No.: 15/878,033

(22) Filed: Jan. 23, 2018

(65) Prior Publication Data
US 2018/0236451 A1    Aug. 23, 2018

Related U.S. Application Data

(63) Continuation of application No. PCT/US2016/044255, filed on Jul. 27, 2016.

(60) Provisional application No. 62/199,069, filed on Jul. 30, 2015.

(51) Int. Cl.
B01L 7/00 (2006.01)
B01L 3/00 (2006.01)
C12Q 1/686 (2018.01)

(52) U.S. Cl.
CPC ........... B01L 7/52 (2013.01); B01L 3/502707 (2013.01); C12Q 1/686 (2013.01);
(Continued)

(58) Field of Classification Search
CPC ...... B01L 7/52; B01L 7/54; B01L 7/00; B01L 3/502707; B01L 2300/1827; B01L 2300/1861; B01L 2300/0893; B01L 2300/0654; B01L 2300/0819; B01L 2300/1822; C12Q 1/686; B01N 21/0332; B01N 2021/0325; B01N 2021/062; G01N 21/6428; G01N 21/6454
See application file for complete search history.

(56) References Cited

U.S. PATENT DOCUMENTS

2003/0143114 A1*   7/2003   Andersson .............. B29C 59/16
                                                        422/64
2004/0067051 A1    4/2004   Kylberg
(Continued)

FOREIGN PATENT DOCUMENTS

EP      2316569 A1      5/2011
JP      2004156925 A    6/2004
WO      2016115542      7/2016

OTHER PUBLICATIONS

Cortie et al. "Plasmonic heating of gold nanoparticles and its exploitation" Proceedings of SPIE. Feb. 28, 2005. doi: 10.1117/12.582207 (Year: 2005).*

(Continued)

*Primary Examiner* — Michael L Hobbs
(74) *Attorney, Agent, or Firm* — O'Banion & Ritchey LLP; John P. O'Banion

(57) ABSTRACT

An LED-driven optical cavity PCR system and method is disclosed for fast, accurate and reliable PCR based diagnostics. An optical cavity comprising two thin light absorbing metal (AU) films is used for uniform light absorption and subsequent photo thermal light-to-heat conversion is employed for PCR thermal cycling.

9 Claims, 11 Drawing Sheets

(52) U.S. Cl.
CPC ............... *B01L 2300/0893* (2013.01); *B01L 2300/1827* (2013.01); *B01L 2300/1861* (2013.01)

(56) References Cited

U.S. PATENT DOCUMENTS

| | | | |
|---|---|---|---|
| 2008/0280776 A1 | 11/2008 | Bashir | |
| 2010/0255487 A1* | 10/2010 | Beechem | C07H 19/20 435/6.12 |
| 2014/0073013 A1 | 3/2014 | Gorman | |
| 2014/0113281 A1* | 4/2014 | Hubbell | C12Q 1/6869 435/6.1 |
| 2015/0141268 A1 | 5/2015 | Rothberg | |
| 2016/0060681 A1* | 3/2016 | Chung | C12Q 1/686 |

OTHER PUBLICATIONS

European Patent Office (EPO), Communication (the extended European search report) dated Jan. 30, 2019, related European patent application No. 16831290, pp. 1-9, claims searched, pp. 10-13.

Corte, Michael B. et al., "Plasmonic heating of gold nanoparticles and its exploitation", Proceedings of SPIE, vol. 5649, Dec. 12, 2004, p. 565-573.

ISA/US, United States Patent and Trademark Office, International Searchh Report and Written Opinion dated Oct. 21, 2016, related PCT international application No. PCT/US2016/044255, pp. 1-11, with claims searched, pp. 12-16.

Yu, Yingjie et al., "Quantitative polymerase chain reaction using infrared heating on a microfluidic chip", Anayitcal Chemistry, vol. 84. No. 6, Mar. 20, 2012, pp. 2825-2829.

Son, Jun Ho et al., "Ultrafast photonic PCR", Light: Science & Applications (2015) 4, pp. 1-7, published online Jun. 29, 2015.

European Patent Office (EPO), Communication pursuant to Article 94(3) EPC dated Nov. 11, 2019, related European paent application No. 16831290.8, pp. 1-5, claims examined, pp. 6-9.

Japan Patent Office (JPO), official action issued May 26, 2020, related Japanese patent application No. 2018-503770, pp. 1-3, English-language translation, pp. 4-6, claims examined, pp. 7-11.

National Intellectual Property Administration (CNIPA), Notification of the First Office Action issued May 19, 2020, related Chinese patent application No. 201680049015.4, pp. 1-9, English-language translation, pp. 10-21, claims examined, pp. 22-26.

* cited by examiner

OPTICAL CAVITY PCR

CROSS-REFERENCE TO RELATED APPLICATIONS

This application is a 35 U.S.C. § 111(a) continuation of PCT international application number PCT/US2016/044255 filed on Jul. 27, 2016, incorporated herein by reference in its entirety, which claims priority to, and the benefit of, U.S. provisional patent application Ser. No. 62/199,069 filed on Jul. 30, 2015, incorporated herein by reference in its entirety. Priority is claimed to each of the foregoing applications.

The above-referenced PCT international application was published as PCT International Publication No. WO 2017/019768 on Feb. 2, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to nucleic acids amplification systems and more particularly to Polymerase Chain Reaction (PCR) thermal cycling systems for medical diagnostic and life science.

2. Background Discussion

There is an urgent need for rapid and accurate diagnostics due to global outbreaks of deadly diseases such as Ebola virus disease (EVD), Middle East Respiratory Syndrome corona virus (MERS-CoV), and human infection with Avian influenza A (H7N9) virus. Polymerase chain reaction (PCR), the "Gold standard" for many medical diagnostic tests, has become an important technique in the fields of clinical laboratories, environmental science, forensic science and agricultural science. Typically PCR, which requires multiple cycles between 2 or 3 discrete temperatures, takes an hour or more per amplification because of the large thermal mass of Peltier based heating blocks as well as slow heat transfer between the heating block and the plastic PCR tube. However, fast/ultrafast PCR is highly desirable for applications such as time-sensitive diagnosis of infectious diseases, methicillin-resistant *Staphylococcus aureus* (MRSA) and sepsis at the point-of-care (POC) level because fast therapeutic turnaround time (TAT) decreases not only the mortality rate but the severe risk for unknowingly transmitting the disease to others.

Commercial PCR systems using air heating/cooling and capillary tubes or direct resistive heating can perform 30 thermal cycles within 10 min. However, these systems are generally not suitable for POC testing due to their high power consumption (800-1000 W maximum) and heavy weight (over 20 kg). For POC testing in resource-limited environments, such as in developing countries or field laboratories, a fast/ultrafast PCR system should be sensitive, selective, portable, robust, simple, easy to use and characterized by low power consumption through miniaturization and integration.

To accomplish these requirements, micro fluidic approaches for fast/ultrafast PCR systems have been extensively investigated to reduce amplification time by decreasing sample volume (i.e. thermal mass), allowing for fast heat transfer, thus faster thermal cycling with less power consumption. The most commonly used method for static micro fluidic PCR thermal cycling is resistive heating with microfabricated thin film heaters and a resistance temperature detector (RTD). While the power consumption is relatively low, this method requires a complicated fabrication process to integrate the thin film heater and RTD on a chip.

A peltier heat block is also widely used for both static and continuous flow PCR due to the rapid heating and cooling rate, but requires higher power consumption. For continuous-flow PCR, PCR amplification occurs when the reaction samples pass thorough discrete temperature zones. This method can produce faster thermal cycling than static PCR, but generally requires an external syringe pump for flow control and lacks the ability to change the cycle number. Another approach includes infrared (IR)-mediated non-contact selective heating of the PCR mixture for PCR thermal cycling using an IR laser or filament lamp, which harnesses the strong IR absorbance by the water at wavelengths over 1000 nm. However, as the volume of the PCR mixture increases from nanoliter to microliter, the total thermal cycling time also increases from ~5 min to ~40 min due to the limitation of fast heating and cooling of PCR solution.

Accordingly, an object of the present description is a fast/ultrafast PCR system for POC testing that is sensitive, selective, portable, robust, simple, easy to use and characterized by low power consumption through miniaturization and integration.

BRIEF SUMMARY

One aspect of the present description is an optical cavity PCR system and method driven by a light-emitting diode (LED) for fast, accurate and reliable PCR based diagnostics. An optical cavity comprising two metallic (e.g. Au) thin films configured for uniform light absorption and subsequent photo thermal light-to-heat conversion is employed for PCR thermal cycling. Simulation results show that temperature differences across the 750 μm-thick cavity are less than 2° C. and 0.2° C. at 94° C. (denaturation) and 68° C. (annealing/extension), respectively. Optical cavity PCR in accordance with the present description shows excellent temperature precision with less than 1° C. temperature variation between cycles and is able to accomplish 30 PCR thermal cycles from 94° C. to 68° C. within 4 min due to low thermal mass and high thermal conductivity of thin Au films.

Using the LED driven optical cavity PCR method of the present description, nucleic acid (c-MET cDNA) amplification was demonstrated with lowest template DNA concentration of $10^{-8}$ ng $\mu L^{-1}$ (2 copies per $\mu L$) within 15 min.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

The embodiments detailed below are directed to an optical cavity for heating a PCR mixture or like substance (Optical Cavity PCR). In the typical PCR sensing process, the PCR mixture generally goes through a plurality of heating and cooling cycles to affect the PCR reaction. Thus, rapid and uniform heating of the target sample (e.g. PCR mixture) is highly beneficial to POC testing. While the embodiments detailed below are directed to PCR-based sensing, it is appreciated that the optical cavity of the present description may be incorporated for use with any process where rapid and uniform heating of a sample is desired.

1. Optical Cavity PCR Configuration

Figure 1A:
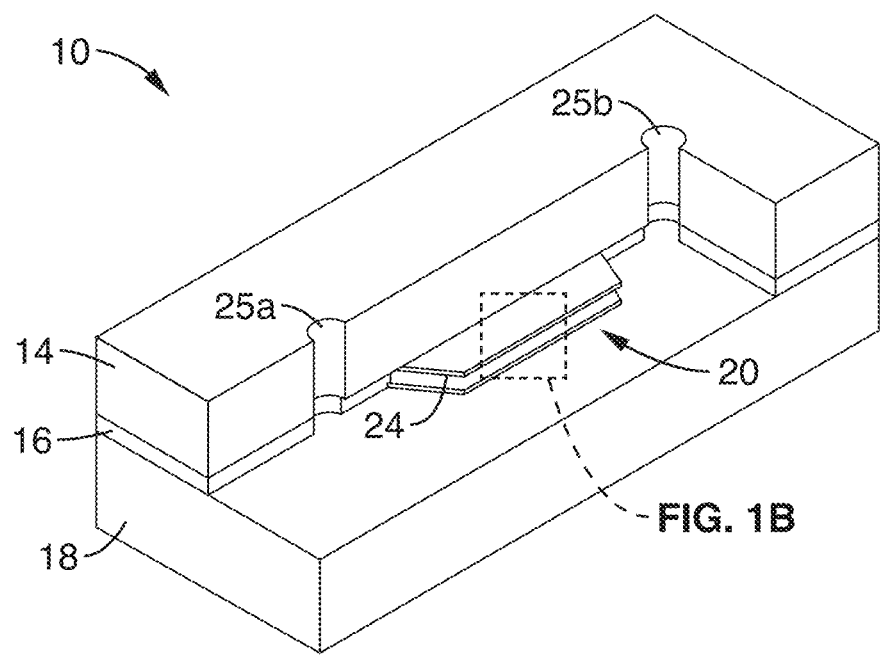
FIG. 1A shows a perspective view of an optical cavity for nucleic acid amplification through polymerase chain reaction (PCR) with top and middle cavity layers partially removed for clarity.
Figure 1B:
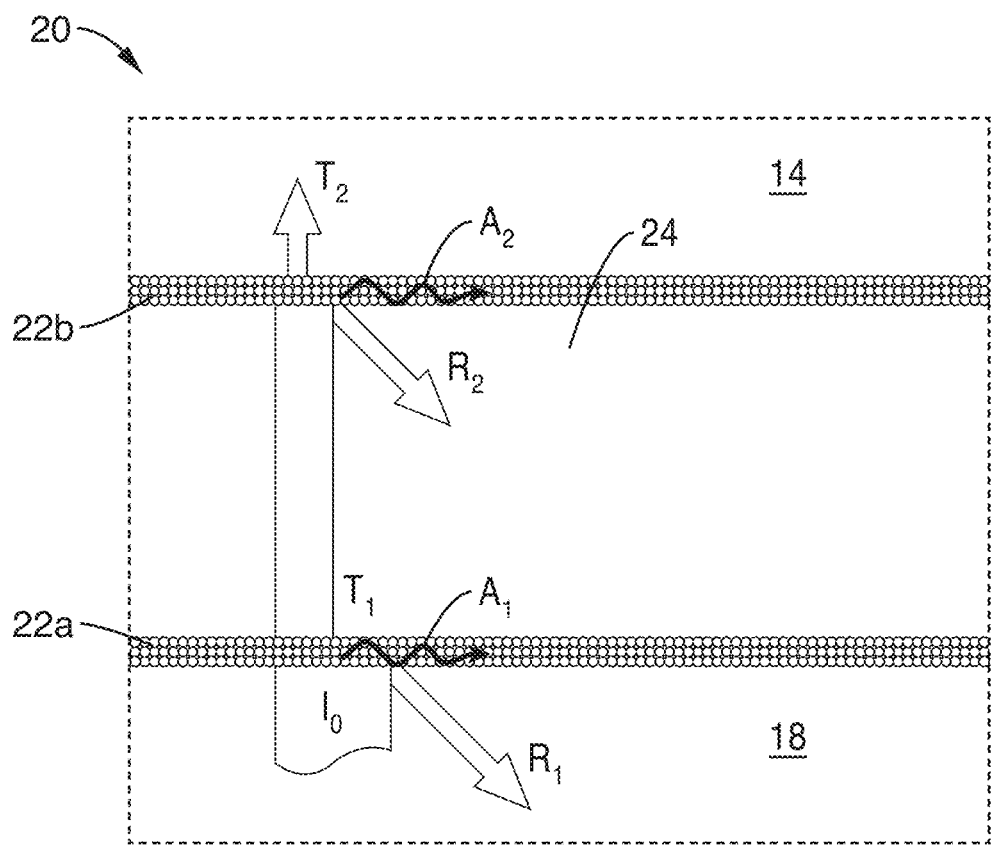
FIG. 1B is a schematic side view of light absorption in the optical cavity of FIG. 1A.

FIG. 1A shows a perspective view of an embodiment of a PCR sensing device 10 comprising an optical cavity 20 for nucleic acid amplification through polymerase chain reaction (PCR) with top and cavity layers partially removed for clarity. FIG. 1B is a schematic side view of the optical cavity 20, showing light absorption and corresponding nucleic acid amplification through polymerase chain reaction (PCR).

In one embodiment, optical cavity 20 comprises two opposing thin film sheets or layers (lower thin film 22a and upper thin film 22b) that are spaced apart to define walls of a micro-fluidic thermal cycling chamber 24, hereinafter referred to as a "PCR chamber" when used for the specific example of holding a PCR mixture for PCR-based testing. Thin films 22a and 22b preferably comprise a light absorbing material or are otherwise configured for absorbing light in a manner so as to provide rapid and uniform heating of the thin films. Both the lower thin film 22a and upper thin film 22b are deposited on respective lower and upper substrate layers 18, 14, respectively. Optical cavity 20 may comprise, for example, a single thermal cycling chamber 24, or an array of chambers for multiplexed amplification.

In a preferred embodiment, one or more of the thin films 22a and 22b comprise Au. However, other materials or compositions may be alternatively employed, e.g., metals such as silver (Ag), nickel (Ni), titanium (Ti), chromium (Cr), germanium (Ge), palladium (Pd), ruthenium (Ru), tungsten (W), iridium (Ir), platinum (Pt), and any alloys composed of the foregoing metals, or a multi-layer metallic structure composed of the foregoing metals or a combination thereof.

Furthermore, the thin film sheets 22a and 22b may comprise a non-metallic, light-absorbing material, including graphene, graphite, carbon nanotubes (CNTs), paint, or the like.

In another embodiment, one or more of lower thin film 22a and upper thin film 22b may be patterned to increase light absorption by resonance. The patterned thin film can be formed on flat polymeric substrate 14, 18, and comprise 2-D or 3-D microstructures or nanostructures in the form of one or more of a pillar array, 1D or 2D grating, photonic crystal, hemi-sphere, or the like.

A middle cavity layer 16 is disposed in between lower and upper substrate layers 18, 14 to define the optical cavity 20 thickness. In a preferred embodiment, lower and upper substrate layers 18, 14 each comprise a transparent polymer, such as acrylic glass, e.g., poly methyl methacrylate (PMMA) or like substance that allows transmission of light.

According to a preferred embodiment, the lower and upper substrate layers 18, 14 preferably comprise a transparent or translucent composition to allow light to pass through to the optical cavity 20. While the lower and upper substrate layers 18, 14 are detailed throughout the description as generally comprising PMMA, it is appreciated that such selection of materials is for exemplary purposes only, and any number of polymeric or translucent/transparent materials may be selected for use as a platform for the thin films. The lower and upper substrate layers 18, 14 may also comprise 2D or 3D microstructures or nanostructures that may comprise one or more of a pillar array, 1D or 2D grating, photonic crystal, hemi-sphere, or other patterned or random structures (not shown). In one embodiment, the lower and upper substrate layers 18, 14 comprise nanoplasmonic structures or nanoplasmonic a feedback laser cavity on the surface of the wells that are configured to be illuminated at a resonance wavelength of nanoplasmonic structures and duration that causes plasmonic photothermal heating of the nanoplasmonic structures.

As seen in FIG. 1A, a pair of ports 25a, 25b are in communication to the optical chamber 20 through the upper substrate layer 14 and middle cavity layer. The ports 25a, 25b allow dispensing of the specimen or sample (e.g. PCR mixture). In one embodiment, the PCR mixture is injected in a first port 25a such that the PCR mixture fills PCR chamber 24. The second port 25b allows air to be pushed out of the chamber until the PCR mixture seals the entire chamber and also exits out second port 25. One or more fluidic valves and/or fluidic control devices (both not shown) may be employed to facilitate filling the PCR chamber 24.

FIG. 1B shows a schematic of light absorption in optical cavity 20 for nucleic acid amplification through polymerase chain reaction (PCR). When a light is illuminated through lower substrate layer 18 (e.g., PMMA) with initial intensity $I_0$, the light is reflected ($R_1$), absorbed ($A_1$), and transmitted ($T_1$) through the lower thin film 22a. Subsequently, the transmitted light ($T_1$) passed through the chamber 24 and is also reflected ($R_2$), absorbed ($A_2$), and transmitted ($T_2$) through the upper thin film 22b. The thin films 22a and 22b act as a plasmonic photo thermal light-to-heat converter for PCR thermal cycling. The absorbed light $A_1$, $A_2$ contributes to the photo thermal heating of the thin film (e.g., Au) atoms for the thermal cycling of PCR.

Figure 1C:
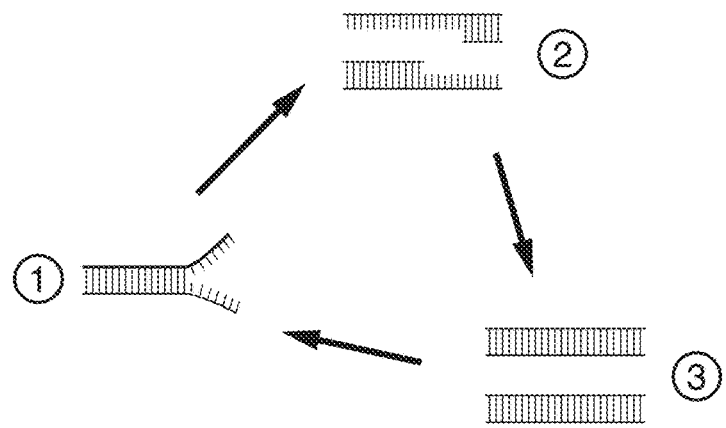
FIG. 1C shows a schematic diagram of corresponding nucleic acid amplification through polymerase chain reaction (PCR) for the cavity of FIG. 1A.

FIG. 1C illustrates an embodiment of the PCR process of denaturation, annealing/extension, and copy (amplification) stages that occurs upon heating of the thin films.

In a first step (1), the process includes illuminating the thin films 22a and 22b with a light for a specified duration, which affects a uniform amount of light absorption into the thin films 22a and 22b and accompanying heating of the thin films 22a and 22b, thereby raising the temperature of a fluid sample (e.g., PCR mixture) in the chamber 24 to a selected temperature for a first period to affect denaturation within the PCR mixture.

In a second step (2), the thin films 22a and 22b are again illuminated with the input light for a specified duration, thereby raising the temperature of a fluid sample (e.g., PCR mixture) in the chamber 24 to a selected temperature for a second period to affect annealing/extension within the PCR mixture.

In a third step (3), the thin films 22a and 22b are again illuminated with the input light for a specified duration, thereby raising the temperature of a fluid sample (e.g. PCR mixture) in the chamber 24 to a selected temperature for a third period to affect copying/amplification within the PCR mixture.

In one embodiment, the three steps are repeated for approximately 30 to 40 cycles.

Based on this model, the total absorption of the Au film 1 and 2 are then given by Eq. 1 and Eq. 2:

$$\sum A_{film1} = I_0 A_1 \left(1 + \frac{T_1 R_2}{1 - R_1 R_2}\right), \quad \text{Eq. 1}$$

$$\sum A_{film2} = I_0 A_2 \left(\frac{T_1}{1 - R_1 R_2}\right), \quad \text{Eq. 2}$$

where $I_0$ is the initial intensity of the light from LED, $A_1$ (and $A_2$), $T_1$ (and $T_2$) and $R_1$ (and $R_2$) are the absorbance, transmittance and reflectance of the thin film 22a (and 22b), respectively.

The thicknesses of the Au films are optimized to have uniform light absorption at both thin films ($\Sigma A_{film1} = \Sigma A_{film2}$) for the greatest uniform temperature distribution as well as the greatest total light absorption ($\Sigma A_{film1} + \Sigma A_{film2}$). First, the average transmittance, reflectance and absorbance of thin Au films 22a, 22b over the emission wavelength of the LED is calculated from the measured absorption spectra of thin Au films with different thickness and emission spectrum of the LED. (See Table 2). Then, the absorption ratio ($\Sigma A_{film1}/\Sigma A_{film2}$) and total absorption ($\Sigma A_{film1} + \Sigma A_{film2}$) are calculated for different combination of top and bottom Au thickness as shown in Table 1. The combination of a 10 nm thickness for the Au thin film 22a, and a 120 nm thickness for the Au thin film 22b was found to be optimal for both the absorption ratio (1.06) and the total absorption of light (70%), which in a preferred configuration may be used as the thicknesses of the thin Au films for the optical cavity 20.

It is also appreciated that alternative materials may be used for tuning the absorption of the thin films 22a, 22b. For example, lower thin film 22a may be comprised of a material that is less absorptive (with more transmission characteristics) than upper thin film 22b. Thus, geometry and/or material composition may be used to tune the absorptive properties of the thin films 22a, 22b.

Figure 2A:
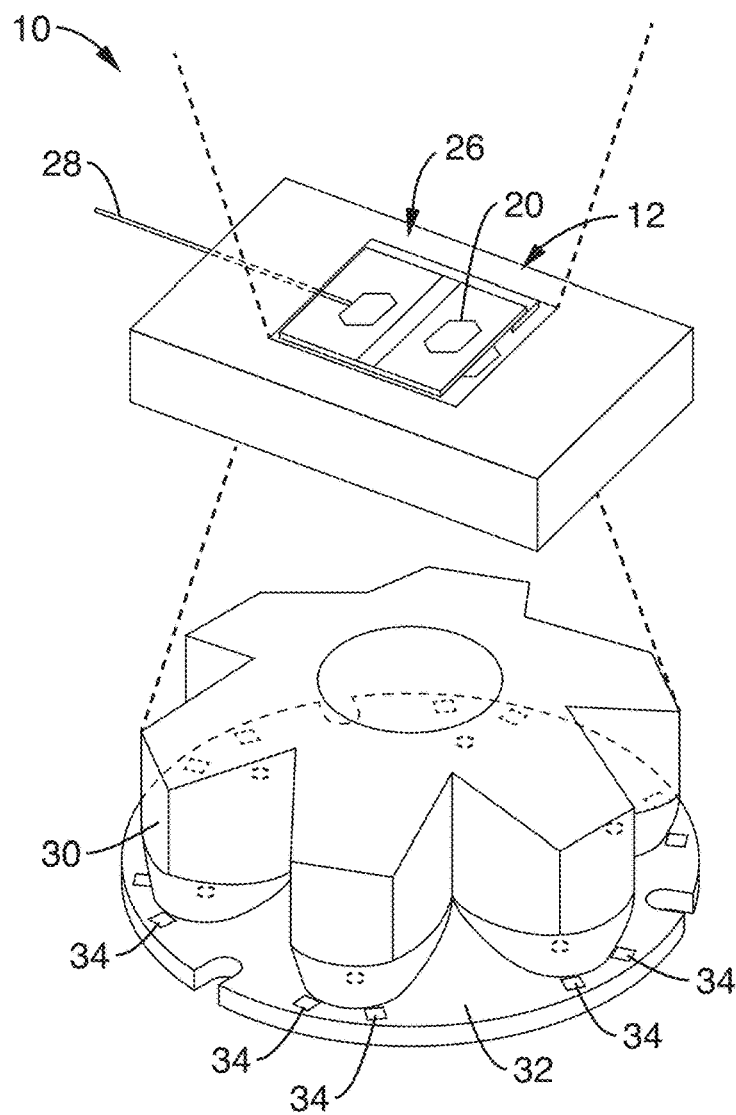
FIG. 2A shows a schematic perspective view of the optical cavity PCR device of FIG. 1A with an LED light source.
Figure 2B:
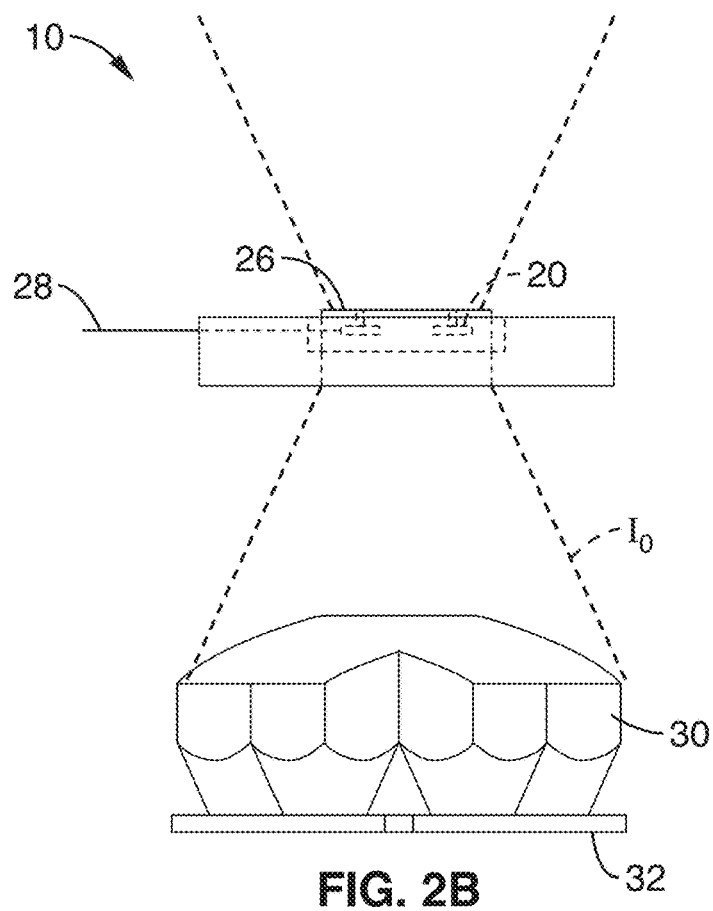
FIG. 2B shows a schematic side view of the LED-driven optical cavity PCR device of FIG. 2A.

FIG. 2A shows a schematic perspective view of the optical cavity PCR device 10 with an illumination or light source. FIG. 2B shows a schematic side view of the optical cavity PCR device 10. The light source is shown as a series of LEDs 34 (e.g., 7 Luxeon Rebel royal blue, LEDS with peak wavelength of 447.5 nm, 6230 mW at 700 mA injection current) disposed on a platform 32 (e.g., 40 mm round cool base), along with a lens 30 for directing input light $I_0$ toward the optical cavity 20. Alternative light sources may include: a laser diode (LD), tungsten lamp, fluorescent lamp, halogen lamp, mercury lamp, xenon lamp, metal halide lamp, or any combination of the foregoing. It is also appreciated that selection of the type of light source, and/or wavelength or intensity of the input light $I_0$, may have an effect on the resonant frequency of the thin films 22a and 22b, and thus thickness and material selection of the thin films 22a and 22b may vary depending on the nature of the input light $I_0$.

A reference chamber 26 with type-K thermocouple 28 is placed next to the optical cavity 20. The reference chamber 26 and optical cavity 20 are configured to be covered by the input light beam $I_0$ waist (e.g., ø=12 mm) at the focal length of the lens 30 to ensure both optical cavity 20 and reference chamber 26 receive the same intensity of light such that photo thermal heating would occur at the same rate. Both optical cavity 20 and reference chamber 26 are placed at the focal length of the lens 30 (e.g., 25 mm away from the top surface of lens in this configuration) for highest light absorption. In one embodiment, the lens 30 comprises a Polymer Optics 7 Cell Cluster Concentrator Optic array.

It is appreciated that the reference chamber 26 is employed in the configuration of FIG. 2A for purposes of providing a reference for temperature in the chamber. However, in a preferred configuration for POC testing, the device of the present description may only include optical cavity 20, or a plurality or array of multiplexed optical cavities, without a reference chamber 26. In such case, feedback regarding the chamber 24 temperature may be obtained via a temperature sensor (not shown) or other sensing means.

Figure 3:
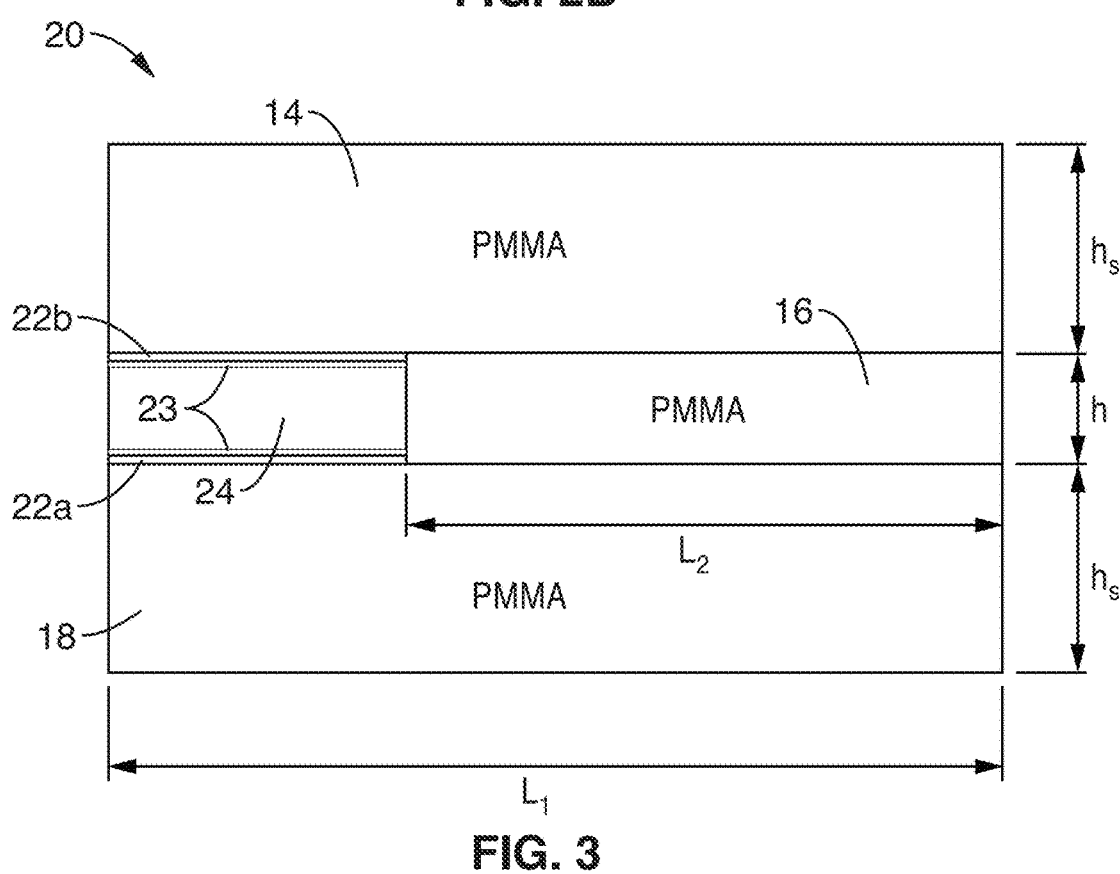
FIG. 3 shows an expanded side view of the layering of the optical cavity of FIG. 1A.

FIG. 3 shows a close up view of the layering of the optical cavity and substrate layers. In one embodiment, each of the thin films 22a and 22b are covered with a passivation layer 23 to prevent PCR reaction inhibition by the metal layer or light absorbing materials. The passivation 23 layer may comprise an oxide thin film, a thin polymer layer, a thin protein layer, or the like. The middle cavity layer 16 has a height h, and upper and lower PMMA layers 14, 18 have a height, $h_s$. In one exemplary embodiment used for testing the apparatus of the present description, $h_s$=1.4 mm, $L_1$=6 mm, $L_2$=4 mm (for a total cavity length of 4 mm) and cavity thickness h was varied from 100 µm, 200 µm, 400 µm, and 750 µm. While the above dimensions are illustrative of one potential embodiment, it is appreciated that other configurations are contemplated.

For the tests described in further detail below, a National Instruments (NI) 9213 16-channel thermocouple module with high speed mode, auto zero and cold junction compensation (not shown) was used for accurate temperature acquisition from the type-K thermocouple 28. Temperature cycling was performed using the LED's 34, an 80 mm cooling fan (not shown), source meter (not shown), and thermocouple 28 all controlled through the LabVIEW program.

In one exemplary configuration, 1 mm-thick poly(methyl methacrylate) (PMMA) sheets were used for the top and bottom substrate layers 14, 18 of the optical cavity 20 as well as 100, 200, 400, and 750 µm-thick PMMA sheets for the middle cavity layer 16 were cut with a VersaLASER VL-200 laser cutting system (Universal Laser System, Inc., Scottsdale, Ariz., USA). The top substrate layer 14 was incubated in an oven at 56° C. for 6 hrs to allow for annealing of damaged regions by laser cutting. The bottom substrate layer 18 and the middle cavity layer 16 were first bonded together using thermal bonding performed at 140° F. with a pressure of 0.2 metric ton after UV/ozone treatment of the PMMA sheet for 10 min. Then, the bottom (bonded with cavity chamber layer) and top layers were cleaned with 70% ethanol twice for 10 min and rinsed with deionized (DI) water and dried using $N_2$. Thin Au films 22a, 22b with different thicknesses (10, 20, 40, 80, and 120 nm) were deposited on the bottom and top PMMA sheets by electron beam (E-beam) evaporation under a base pressure of $2\times10^{-7}$ Torr. A 50 nm-thick $SiO_2$ passivation layer was deposited over the thin Au films 22a, 22b by RF sputtering to prevent PCR reaction inhibition by the thin Au film. Finally, the bottom (bonded with cavity chamber layer) and top layers were bonded together to form optical cavity 20 PCR chamber 24 using thermal bonding performed at 140° F. with a pressure of 0.2 metric ton after UV/ozone treatment of the PMMA sheet for 10 min.

In one embodiment, the optical cavity 20 may be configured for lasing of fluorescent emission during the PCR reaction for real-time optical cavity PCR. Such configuration may provide further enhancement of the sensitivity of real-time cavity PCR compared to conventional real-time PCR.

2. Experimental Results a. Simulation for the Temperature Uniformity of Optical Cavity PCR.

Figure 4A:
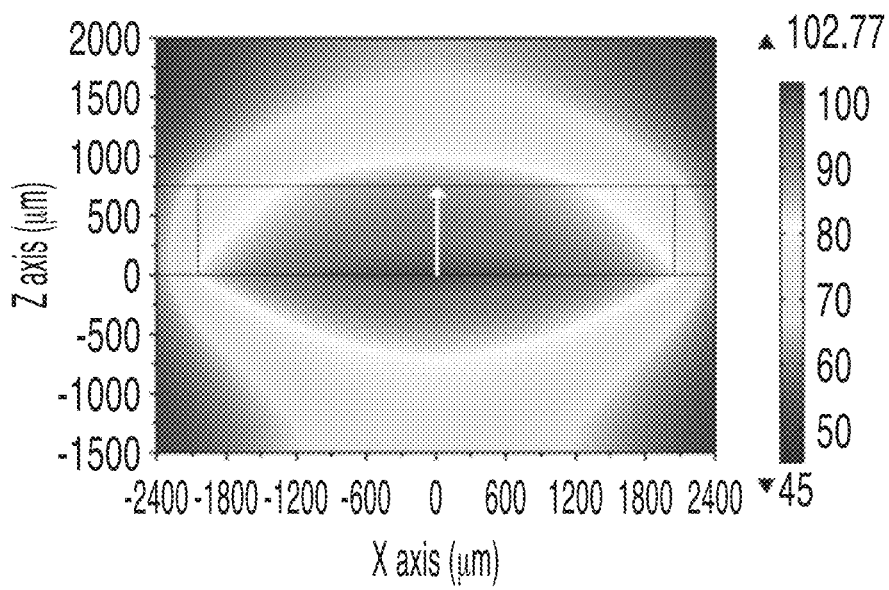
FIG. 4A through FIG. 4D show images of the calculated temperature distribution inside a 750 $\mu m$-thick optical PCR chamber for the bottom only and cavity (top and bottom) heating.
Figure 4B:
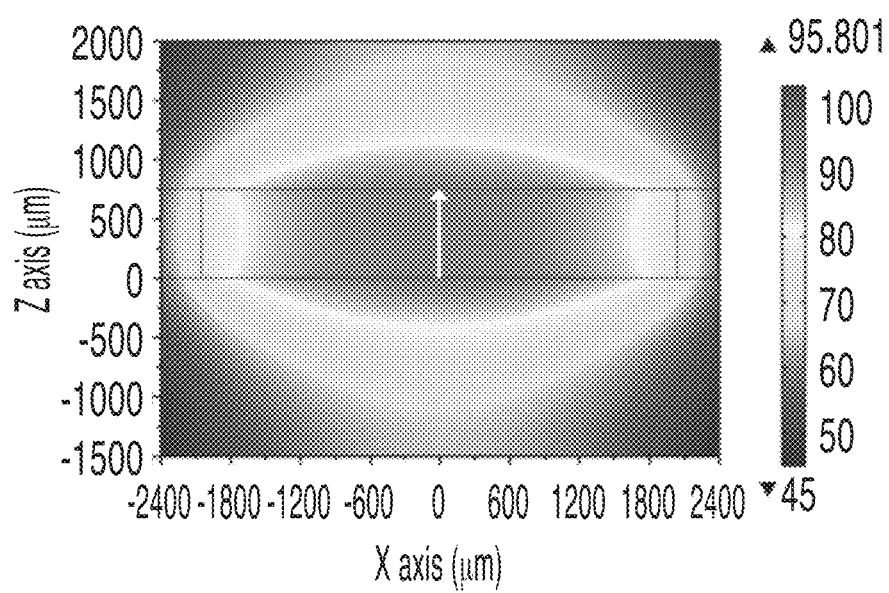
Figure 4C:
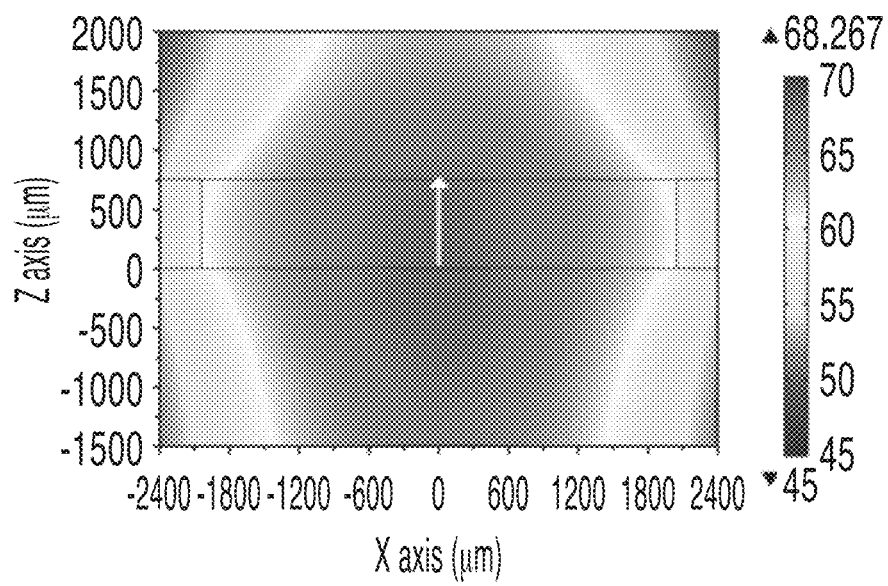
Figure 4D:
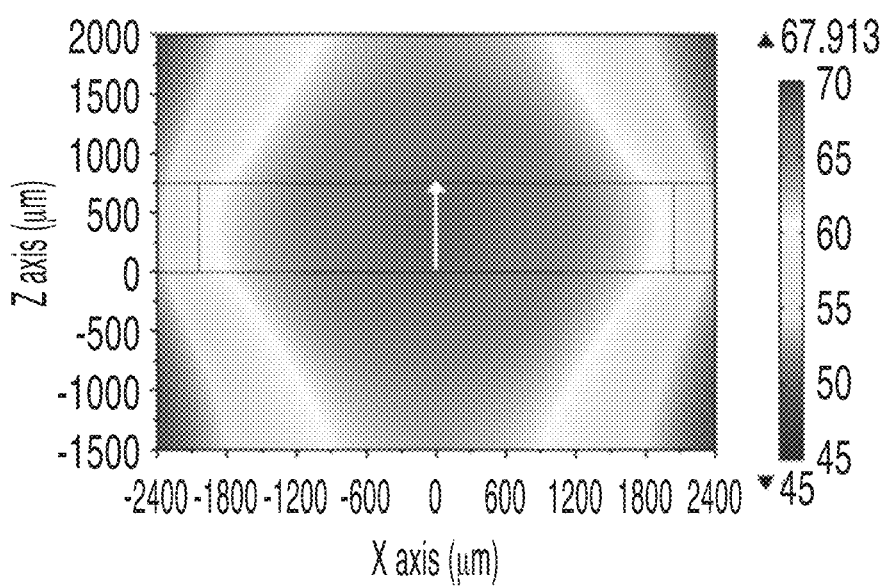

A set of heat transfer simulations using COMSOL were performed to characterize the temperature uniformity inside the optical cavity 20 during PCR thermal cycling. FIG. 4A through FIG. 4D show the calculated temperature distribution inside a 750 µm-thick PCR chamber for the bottom only and cavity (top and bottom) heating. FIG. 4A and FIG. 4C show the calculated temperature distribution for bottom only heating and FIG. 4B and FIG. 4D show the calculated temperature distribution for top and bottom (cavity) heating in the PCR chamber 24 when the temperature at the center of the chamber (0 µm on x-axis and 375 µm on z-axis) reaches 94° C. for denaturation and 68° C. for annealing/extension, respectively.

Figure 5:
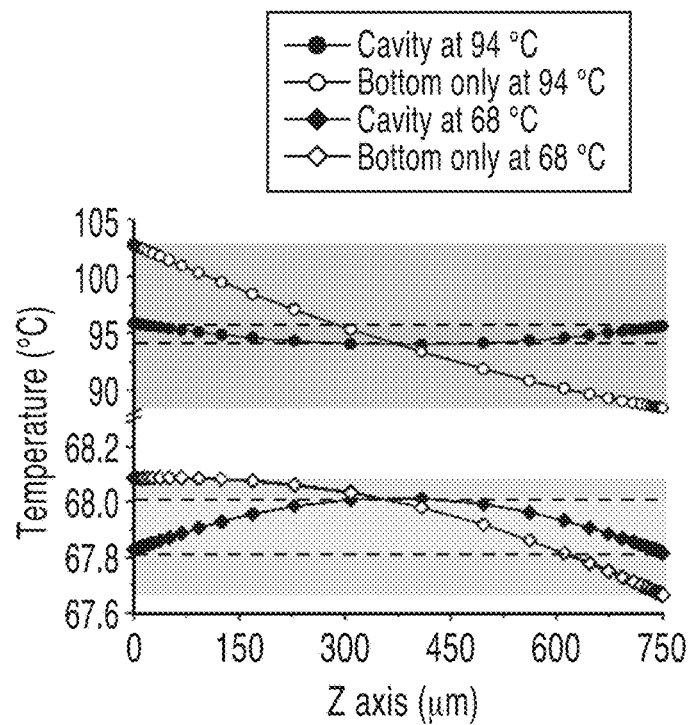
FIG. 5 shows a plot of the temperature profiles of the PCR chambers along the white arrows in FIG. 4A through FIG. 4D.

FIG. 4A through FIG. 4D provide clear illustration that the optical cavity (top and bottom) heating of the device of the present description provides a more uniform temperature distribution compared to bottom only heating, especially at 94° C. The temperature gradients across the height of the chamber (along the white arrow) are plotted in FIG. 5. Cavity heating in accordance with the present description shows better temperature uniformity with a difference of only 1.9° C. and 0.2° C. compared to a temperature difference of 14.4° C. and 0.4° C. for bottom only heating at 94° C. and 68° C., respectively.

Figure 6:
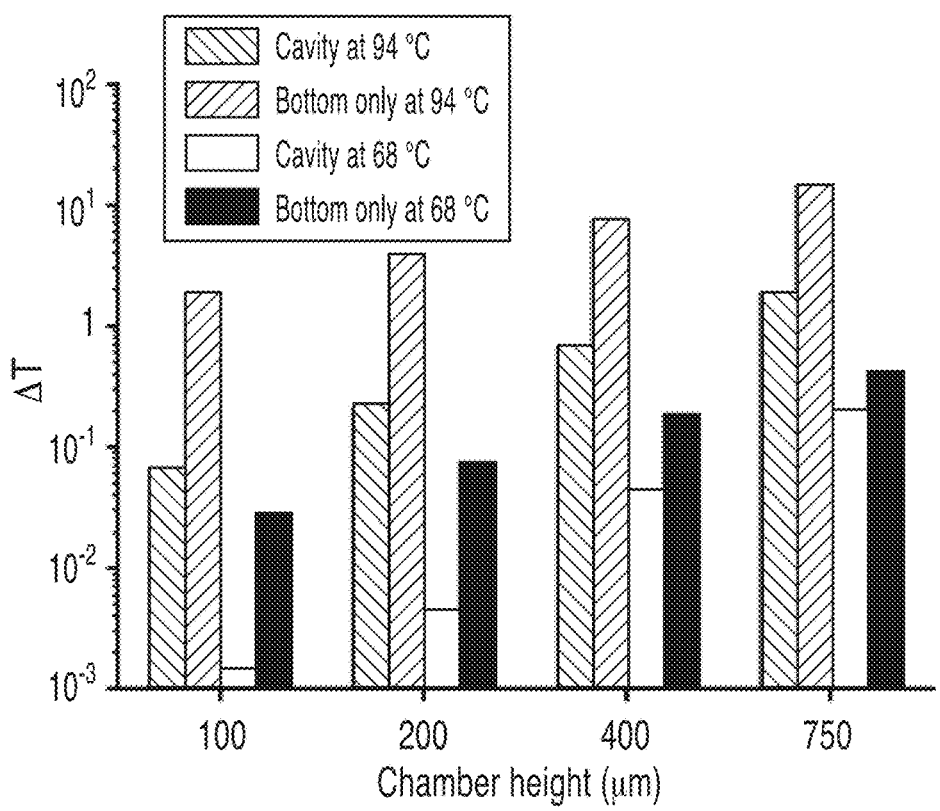
FIG. 6 shows a graph of the temperature difference along the z-axis (0 $\mu m$ on x-axis) of the optical PCR chamber of the present description as a function of PCR chamber height.

Referring to FIG. 6, the effect of PCR chamber height on temperature uniformity was also investigated. As the height of the PCR chamber decreases, the temperature difference ($\Delta T=T_{max}-T_{min}$) across the height of the chamber decreases for both the bottom only and cavity heating configurations, because heat transfer can be more effective for the smaller volume in a thinner PCR chamber. Furthermore, it is noteworthy that cavity heating of the device of the present description shows much smaller temperature differences for all chamber heights at both the denaturation and annealing/extension temperatures. Therefore, employing the cavity heating in accordance with the present description allows for the uniform heating of PCR mixture for efficient and reliable nucleic acids amplification.

b. LED-Driven Optical Cavity PCR Thermal Cycler.

Figure 7:
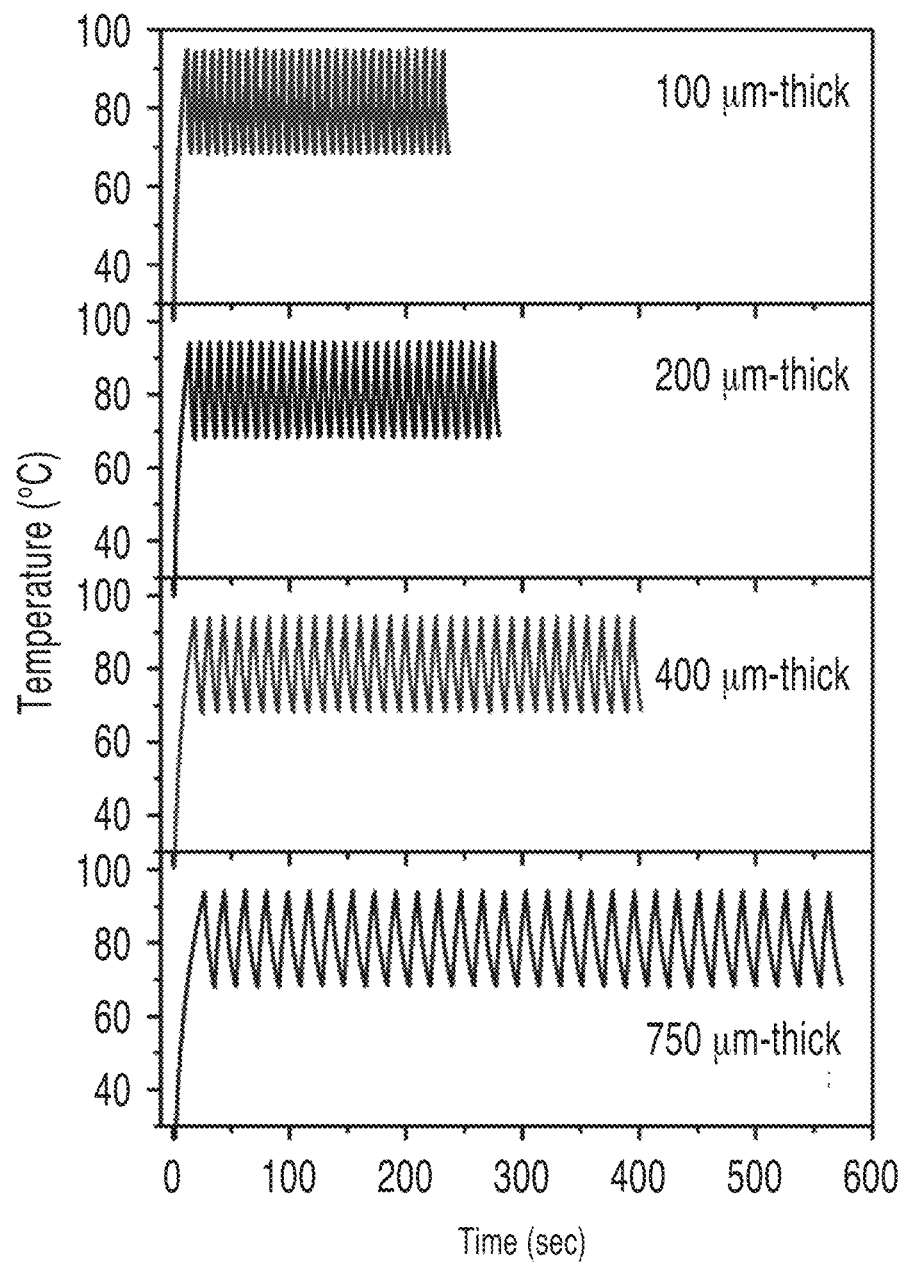
FIG. 7 shows the representative temperature profile for 30 PCR thermal cycles from 94° C. to 68° C. using the LED-driven optical cavity for different chamber heights.
Figure 8A:
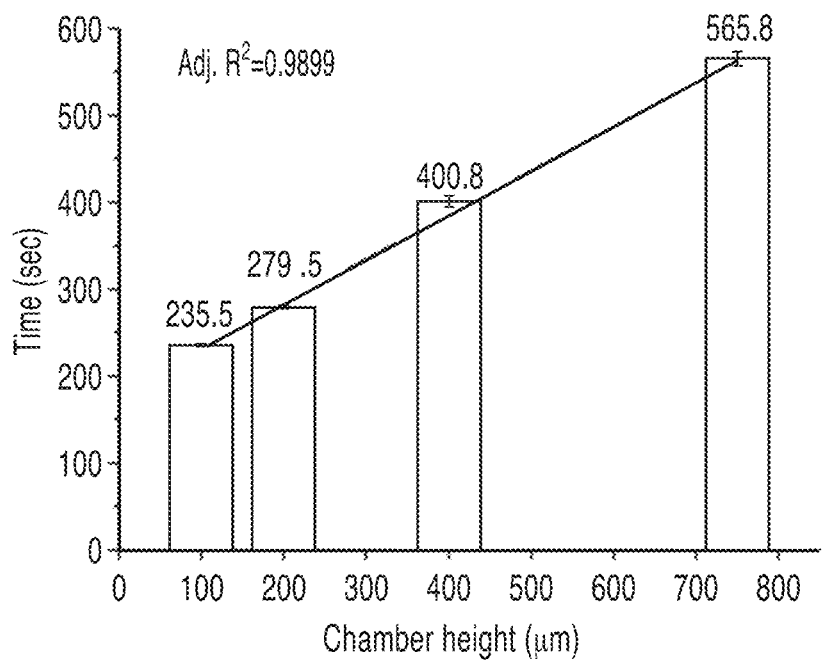
FIG. 8A shows the total reaction time of 30 thermal cycles for the optical cavity PCR device of the present description with varying chamber heights.

FIG. 7 shows the representative temperature profile for 30 PCR thermal cycles from 94° C. to 68° C. using the LED-driven optical cavity for different chamber heights. The total time of 30 PCR cycles decreases as the cavity height h decreases, attaining the minimum time (average 235.5 sec) with a 100 µm-thick optical cavity 20 PCR chamber 24, and showing good linearity with an adjusted $R_2$ value of 0.9899 as shown in FIG. 8A.

Figure 8B:
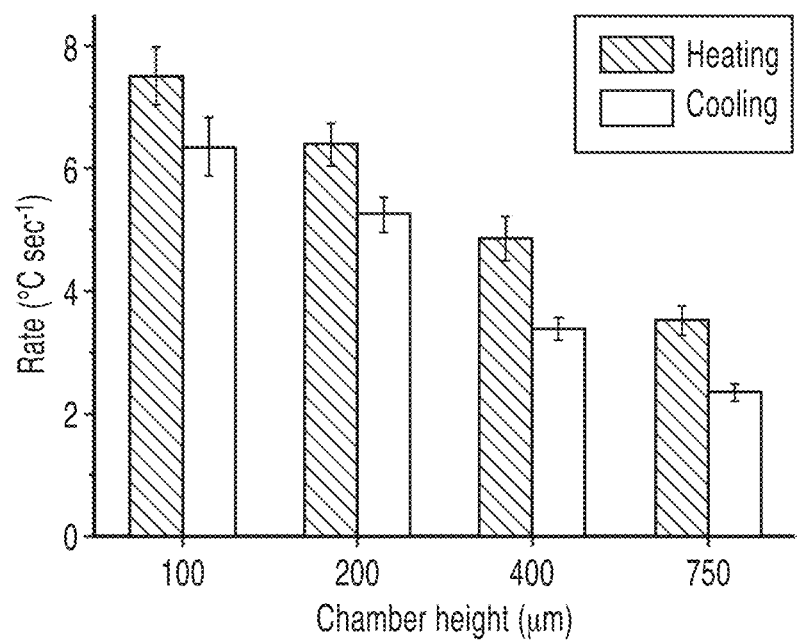
FIG. 8B shows the average rates during 30 PCR cycles and sample standard deviations for different chamber heights.

Using the thermal cycling result, heating and cooling rates were calculated. The average rates during 30 PCR cycles and sample standard deviations were obtained as shown in FIG. 8B. The fastest heating and cooling rates of 7.50±0.46° C. sec$^{-1}$ and 6.35±0.49° C. sec$^{-1}$ were obtained from the 100 µm-thick PCR chamber 24.

Figure 8C:
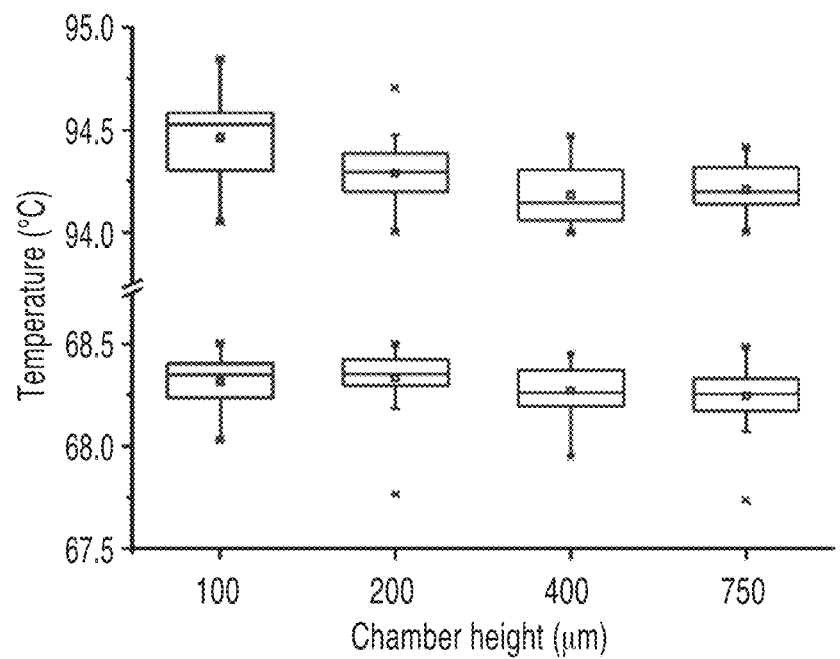
FIG. 8C shows the measured temperature distribution at 94° C. (denaturation) and 68° C. (annealing/extension) during 30 thermal cycles with different chamber height.

FIG. 8C shows the measured temperature distribution at 94° C. (denaturation) and 68° C. (annealing/extension) during 30 thermal cycles with different chamber height. The maximum and minimum temperatures attained during each PCR cycle vary within less than 1° C. at 94° C. and less than 0.5° C. at 68° C., showing comparable temperature accuracy with commercially available bench top thermal cyclers. In particular, due to the lower heat mass as well as fast heat transfer between the thin Au film and PCR mixture through a 50 nm-thick SiO$_2$ layer, the overshoot and undershoot for the cavity PCR are very low (0.85° C. at 94° C., 0.25° C. at 68° C.) compared to the bench top thermal cycler (~2° C. at 94° C. ~4° C. at 68° C.), when fast cycling is performed, because the bench-top thermal cycler is not designed for fast thermal cycling.

Figure 8D:
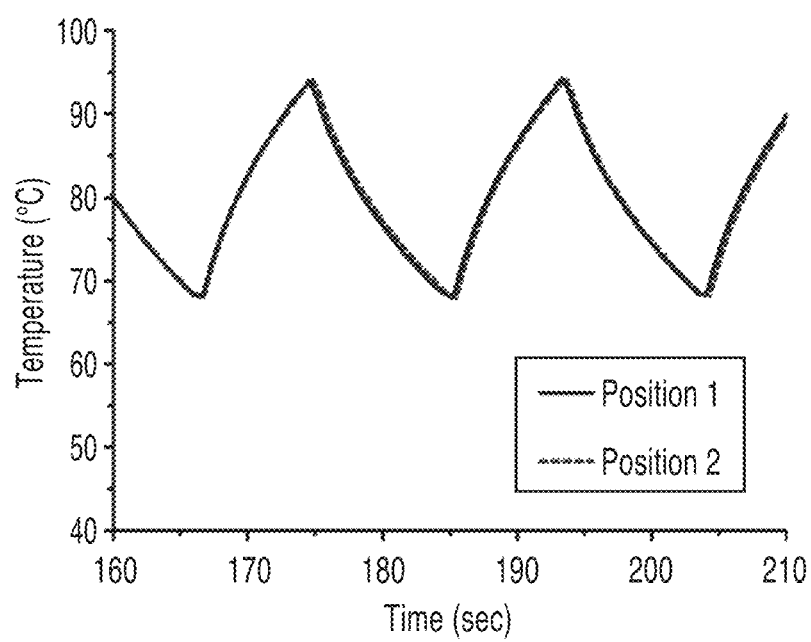
FIG. 8D shows the comparison of temperature profiles during thermal cycling between two positions.

In order to ensure both chambers at position 1 (reference chamber 26) and 2 (optical cavity PCR chamber 24) are heated at the same rate, a reference chamber 26 with type-K thermocouple 28 was placed at both positions and thermal cycling was performed. FIG. 8D shows the comparison of temperature profiles during thermal cycling between position 1 and 2, and it is clearly seen that both positions receive the same intensity of light from the LED for photo thermal heating of thin Au films.

c. Nucleic Acid Amplification Using Optical Cavity PCR.

To verify the LED driven optical cavity PCR system and method of the present description, the amplification of nucleic acids (c-MET cDNA, lung cancer biomarker) was demonstrated.

Human HGFR, or c-MET cDNA was used as a template for PCR. For conventional bench top PCR with recommended concentrations, the PCR reaction consisted of 0.08 µL KAPA2G DNA polymerase, 4 µL 5×KAPA2G buffer A, 0.4 µL dNTP mixture, 1 µL each forward and reverse c-MET primers (stock solution 10 µM), 6.7 µL BSA (3% w/v stock solution for a final concentration of 10 µg µL$^{-1}$ BSA) and 2 µL template cDNA. Water was added to bring the final volume to 20 µL. To increase the amplification efficiency in the fast cycling cavity PCR, high concentration of polymerase and primers were used. The PCR reaction for the cavity PCR consisted of 0.4 µL KAPA2G DNA polymerase, 2 µL of 5×KAPA2G buffer A, 0.2 µL dNTP mixture, 1 µL each forward and reverse c-MET primers (stock solution 100 µM), 3.3 µL of BSA (3% w/v stock solution for a final concentration of 10 µg µL$^{-1}$ BSA) and 1 µL template DNA. Again, water was added until the reaction was brought to a final volume of 10 µL. The concentration of c-MET cDNA also varied, and was brought to as low as 10-8 ng µL$^{-1}$ (2 copies per µL).

The PCR mixture was loaded into the optical cavity 20 PCR chamber 24 using a pipette and a first port 25 until the second port 25 on the other side of the chamber 24 filled with fluid to ensure no air bubbles were formed during thermal cycling. The two ports 25 were sealed with PCR sealing tape to ensure no bubble formation or loss of fluid. The optical cavity 20 was placed in line with the reference chamber 26 with the 120 nm-thick Au film on top, as this is the optimal configuration for uniform light absorption and maximum total absorption of the thin Au films. After amplification, a mixture of 10 µL of PCR product (collected from cavity PCR chamber using pipette) and 10 µL of E-Gel sample loading buffer (Invitrogen) was loaded onto E-Gel 2% agarose gels with SYBR Safe DNA gel stain (Invitrogen) and run in an E-Gel iBase Power System (Invitrogen) and took gel image with E-Gel Safe Imager Transilluminator. A 50 bp DNA ladder was used to confirm the size of the product. A Bio-Rad C1000™ thermal cycler with CFX96 real-time PCR detection system was used for the reference PCR system. PCR was performed in 20 µL volume for the bench top and 5 µL and 10 µL volumes for the cavity PCR with different chamber thickness. In addition to c-MET cDNA, the λ-DNA was also used as a template for PCR for initial cavity PCR optimization. The PCR reaction to amplify a 104-base pair (bp) λ-DNA target with Z-Taq™ DNA polymerase included 0.5 µL Z-Taq DNA polymerase, 5 µL of 10×Z-Taq Buffer, 4 µL of dNTP mixture, 4.5 µL of 10 µM primers (each), and 10 µL of bovine serum albumin (BSA) (50 µg) and was brought to 50 µL with PCR-grade water. The final concentration of the template λ-DNA varied from 0.01 ng µL$^{-1}$ to 10 ng uL$^{-1}$.

Figure 9A:
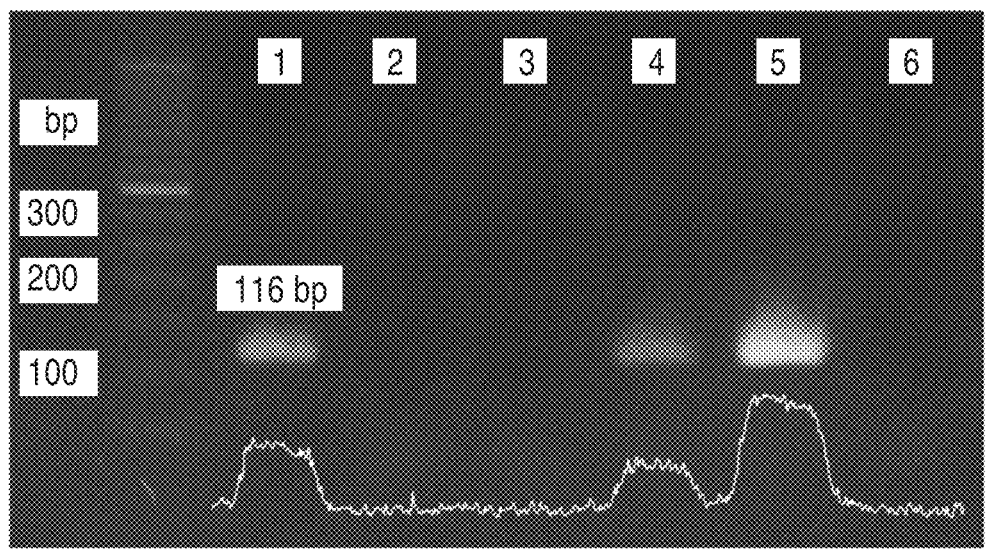
FIG. 9A shows a 2% agarose gel image from the bench-top thermal cycler compared with the optical cavity PCR device of the present description (with a 750 $\mu m$-thick PCR chamber) with different cycle numbers from 95° C. to 68° C.

FIG. 9A shows a 2% agarose gel image from the bench-top thermal cycler (Bio-Rad C1000™ thermal cycler with CFX96 real-time PCR detection system) and cavity PCR (with a 750 µm-thick PCR chamber 24) with different cycle numbers from 95° C. to 68° C. (Point 1: bench top 10$^{-4}$ ng µL$^{-1}$ and 30 cycles, Point 2 bench top NTC Point 3: cavity at 20 cycles, Point 4: cavity at 30 cycles, Point 5: cavity at 40 cycles, Point 5: cavity at NTC).

For the bench-top PCR, a 3-step thermal cycling protocol was used. FIG. 9A shows a clear trend that as cycle number increases the intensity of the band increases for the optical cavity 20.

Figure 9B:
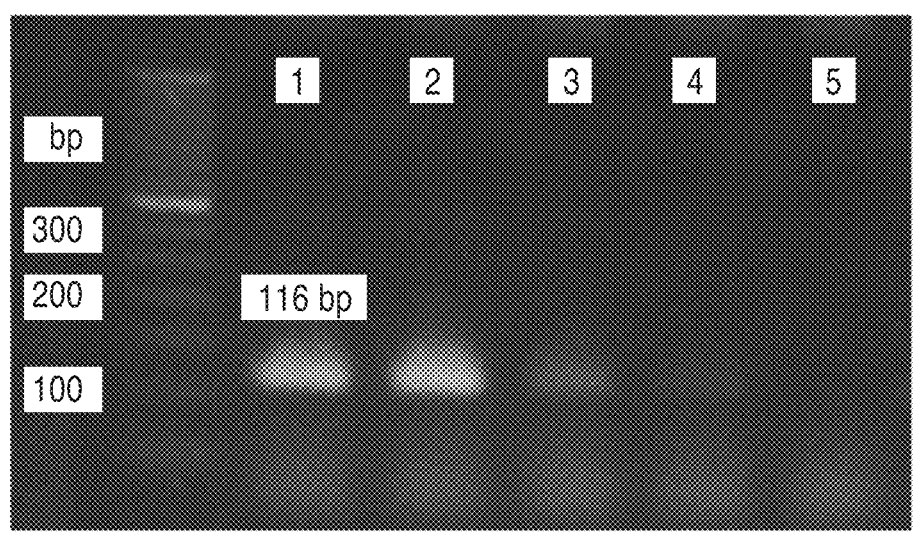
FIG. 9B shows a 2% agarose gel image from the PCR device of the present description with different initial concentrations of template DNA.

FIG. 9B shows the 2% agarose gel image from the cavity PCR product with different initial concentrations of template DNA (Point 1 at 10$^{-5}$ ng µL$^{-1}$, Point 2 at 10$^{-7}$ ng µL$^{-1}$, Point 3 at 10$^{-7}$ ng µL$^{-1}$, Point 4 at 10$^{-8}$ ng µL$^{-1}$, Point 5 at NTC). There is a clear trend in band intensity as the concentration changes. Furthermore, 40 cycles of cavity PCR was able to amplify as low as 10$^{-8}$ ng µL$^{-1}$ (2 copies per µL$^{-1}$) within 15 min.

Figure 10:
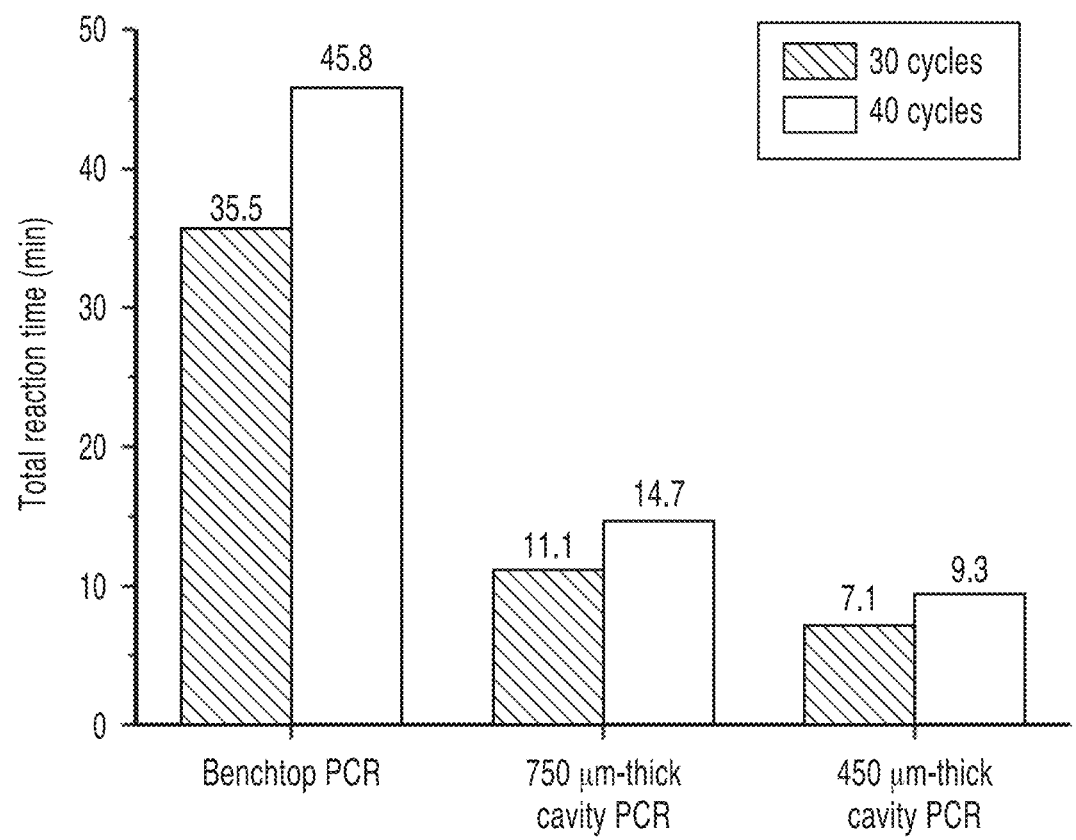
FIG. 10 shows a graph summarizing the total reaction time for the bench-top thermal cycler compared with the optical cavity PCR device of the present description.

The total reaction time for the bench-top and cavity PCR is summarized in FIGS. 10. A 70% to 80% reduction in total reaction time can be obtained by using cavity PCR in accordance with the present description, although the total reaction times for the KAPA2G Fast PCR kit are already 20-70% shorter than conventional PCR assays.

In addition to the fast and sensitive nucleic acid amplification, the optical cavity 20 is highly repeatable and reproducible. The demonstration of a robust LED driven optical cavity PCR makes the system and method of the present description an ideal candidate for implementation into POC platforms that require fast, accurate and reliable nucleic acids amplification.

3. Summary

The optical cavity PCR device 10 of the present description was effective not only in fast PCR thermal cycling, but also in reliable nucleic acid amplification comparable to the conventional bench top PCR system. Providing the test result within 30 min is highly desirable to make a single visit viable. The optical cavity PCR device 10 of the present description can meet this requirement because the device can accomplish 30 PCR thermal cycles within 4 to 10 min and amplify nucleic acid concentrations as low as 10$^{-8}$ ng µL$^{-1}$ (2 copies per µL) within 15 min.

By optimizing the thickness of thin Au films of the optical cavity 20, light absorption can be uniformly absorbed at the top and bottom thin Au layers 22a, 22b of the optical cavity 20, resulting in excellent temperature uniformity with a difference of only 1.9° C. and 0.2° C. at 94° C. and 68° C., respectively. As a result, the optical cavity PCR device 10 of the present description shows excellent repeatability and reproducibility due to the excellent temperature uniformity as well as precise temperature accuracy. Generally, the faster thermal cycling is driven, the greater the variation of the temperature across the PCR sample due to thermal inertia. However, in optical cavity PCR, there is not a significantly large difference in the temperature accuracy with different sample volume ranging from 1.3 µL to 10 µL. This could be attributed to not only the low thermal mass, but also the fast heat transfer between the thin Au film and PCR mixture through the ultrathin 50 nm-thick SiO$_2$ passivation layer.

The power consumption of the tested device was relatively high (~20 W), because 7 LED were used on a single PCB to have wide beam waist for heating the reference and cavity PCR chambers at a same rate. However, by using two 3 W LEDs for each of the reference chamber 26 and optical cavity 20 (or individual optical cavities 20 in a multiplexed configuration), the power consumption may be further reduced (~6 W). The embodiments of the present description are focused on quantitative real-time PCR using fluorescent detection as well as integrating multiple PCR wells and multiple LEDs to allow for high throughput multiplexed amplification.

In conclusion, a novel ultrafast PCR by a LED-driven optical cavity PCR thermal cycler was demonstrated. The thin Au films of different thicknesses on both the top and bottom of the cavity shows increased light-to-heat conversion efficiency and improved temperature uniformity than bottom only heating photonic PCR. When controlled for total amplification time, comparable nucleic acids amplification of the c-MET gene with commercial bench top thermal cycler was demonstrated. Ultrafast amplification of c-MET gene, thermal cycling between 94° C. (denaturation) and 68° C. (annealing/extension) was achieved within 4-10 minutes for 30 cycles with ultrafast heating. In addition, we demonstrated repeatability and reproducibility of our cavity PCR platform. We propose that this simple and robust ultrafast cavity PCR thermal cycler is suitable for POC diagnostics.

From the description herein, it will be appreciated that that the present disclosure encompasses multiple embodiments which include, but are not limited to, the following:

1. An apparatus for thermal cycling of a fluidic sample, the apparatus comprising: at least one micro-fluidic thermal cycling chamber, said chamber defined by a plurality of chamber walls configured to hold the fluidic sample; a first thin film disposed on a first substrate to define a first chamber wall of the thermal cycling chamber; a second thin metal film disposed on a second substrate to form a second chamber wall opposite the first chamber wall; and a light source configured to illuminate the first thin film; wherein a first portion of light illuminated onto the first thin film is absorbed into the first thin film and a second portion of the light illuminated onto the first thin film is transmitted through the first thin film; wherein the light transmitted through the first thin film illuminates the second thin film; wherein at least a portion of the transmitted light illuminated onto the second thin film is absorbed into the second thin film; and wherein the absorbed light into the first thin film and second thin film are configured to elevate the temperature of the first thin film and second thin film to heat the fluidic sample within the thermal cycling chamber.

2. The apparatus of any preceding embodiment, wherein one or more of the first thin film and second thin film comprise a metallic layer.

3. The apparatus of any preceding embodiment, wherein the metallic layer comprises a metal selected from the group consisting of: gold (Au), silver (Ag), nickel (Ni), titanium (Ti), chromium (Cr), germanium (Ge), palladium (Pd), ruthenium (Ru), tungsten (W), iridium (Ir), or platinum (Pt).

4. The apparatus of any preceding embodiment: wherein one or more of the first thin film and second thin film comprise a multi-layer metallic structure; and wherein the metallic structure comprises one or more metals selected from the group consisting of: gold (Au), silver (Ag), nickel (Ni), titanium (Ti), chromium (Cr), germanium (Ge), palladium (Pd), ruthenium (Ru), tungsten (W), iridium (Ir), or platinum (Pt).

5. The apparatus of any preceding embodiment, wherein one or more of the first thin film and second thin film comprise a non-metallic light absorbing material selected from the group consisting of: graphene, graphite, carbon nanotubes (CNTs), or paint.

6. The apparatus of any preceding embodiment, wherein one or more of the first thin film and second thin film comprise a patterned surface to increase light absorption by resonance.

7. The apparatus of any preceding embodiment, wherein one or more of the first substrate and second substrate comprise a translucent material configured to allow transmission of the illuminated light through at least the first substrate to the first thin film.

8. The apparatus of any preceding embodiment, wherein one or more of the first substrate and second substrate comprise 2-D or 3-D microstructures or nanostructures in the form of one or more of a pillar array, 1D or 2D grating, photonic crystal, or hem i-sphere.

9. The apparatus of any preceding embodiment, wherein the first thin film has a first thickness, and the second thin film has a second thickness different than the first thickness.

10. The apparatus of any preceding embodiment, wherein the first thin film thickness and second thin film thickness are selected so as to match a rate of absorption of light into the first thin film and second thin film such that the first thin film and second thin film have a substantially uniform rate of temperature elevation.

11. The apparatus of any preceding embodiment, further comprising at least one temperature sensor configured to sense the temperature within the thermal cycling chamber.

12. The apparatus of any preceding embodiment, wherein the first thin film and second thin film have a surface covered with passivation layer to prevent PCR reaction inhibition within the thermal cycling chamber.

13. The apparatus of any preceding embodiment, wherein the light source is selected from the group consisting of: a light-emitting diode (LED), laser diode (LD), tungsten lamp, fluorescent lamp, halogen lamp, mercury lamp, xenon lamp, metal halide lamp, or combination thereof.

14. The apparatus of any preceding embodiment, further comprising: first and second ports coupled to the thermal cycling chamber; wherein the first and second ports are configured to allow input of the fluidic sample into the thermal cycling chamber.

15. A method for performing ultra fast thermal cycling of a fluidic sample, the method comprising: providing a micro fluidic thermal cycling chamber defined by opposing first and second thin films; filling the thermal cycling chamber with the fluidic sample; illuminating the first thin film with a light source; wherein a first portion of light illuminated onto the first thin film is absorbed into the first thin film and a second portion of the light illuminated onto the first thin film is transmitted through the first thin film; illuminating the second thin film with the light transmitted through the first thin film; wherein at least a portion of the transmitted light illuminating the second thin film is absorbed into the second thin film; uniformly elevating the temperature of the first thin film and second thin film as a function of the absorbed light into the first thin film and second thin film; and heating the fluidic sample within the thermal cycling chamber as a result of the elevated temperature of the first thin film and second thin film.

16. The method of any preceding embodiment, wherein illumination of the first thin film is intermittently applied to perform ultra fast micro-fluidic polymerase chain reaction (PCR) of the fluidic sample.

17. The method of any preceding embodiment, wherein uniformly elevating the temperature of the first thin film and second thin film comprises: illuminating the first and second films for a first duration to raise the temperature of the fluid sample in the thermal cycling chamber to a selected temperature for a first period; illuminating the first and second films for a second duration to raise the temperature of the fluid sample in the thermal cycling chamber to a selected temperature for a second period; illuminating the first and second films for a third duration to raise the temperature of the fluid sample in the thermal cycling chamber to a selected temperature for a third period; and repeating a cycle of illumination periods for multiple cycles to amplify the fluid sample.

18. The method of any preceding embodiment, wherein the first thin film has a first thickness, and the second thin film has a second thickness different than the first thickness.

19. The method of any preceding embodiment, wherein the first thin film thickness and second thin film thickness are selected so as to match a rate of absorption of light into the first thin film and second thin film such that the first thin film and second thin film have a substantially uniform rate of temperature elevation.

20. The method of any preceding embodiment, further comprising: measuring a temperature within the thermal cycling chamber.

21. The method of any preceding embodiment, wherein the first thin film and second thin film have a surface covered with a passivation layer to prevent PCR reaction inhibition within the thermal cycling chamber.

22. The method of any preceding embodiment, wherein filling the thermal cycling chamber with the fluidic sample comprises: injecting fluidic sample into the cycling chamber through a first port coupled to the thermal cycling chamber; wherein the injected fluid sample pushes air out of a second port coupled to the thermal cycling chamber.

23. The method of any preceding embodiment wherein the optical cavity is configured for lasing of fluorescent emission during the PCR reaction.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Optimization of Au film in optical cavity PCR chamber

| Ratio/ Total absorption | | Au Film (nm) | | | | |
|---|---|---|---|---|---|---|
| | | 10 | 20 | 40 | 80 | 120 |
| Au Film (nm) | 10 | 2.10/0.48 | 1.64/0.56 | 1.32/0.63 | 1.06/0.69 | 1.04/0.70 |
| | 20 | 4.44/0.51 | 3.36/0.56 | 2.64/0.61 | 2.14/0.65 | 2.09/0.65 |
| | 40 | 15.34/0.54 | 11.21/0.56 | 8.58/0.58 | 7.00/0.59 | 6.84/0.60 |
| | 80 | 174.78/0.62 | 126.47/0.62 | 96.13/0.62 | 78.57/0.63 | 76.77/0.63 |
| | 120 | 1970.97/0.63 | 1425.4/0.63 | 1082.9/0.63 | 885.19/0.63 | 864.94/0.63 |

TABLE 2

Averaged transmittance, reflectance and Absorptance of the thin Au film over emission wavelength of LEDs with different thickness

| Au thickness | T (%) | R (%) | A (%) |
|---|---|---|---|
| 10 nm | 50.6 | 19.7 | 29.7 |
| 20 nm | 29.6 | 31.2 | 39.2 |
| 40 nm | 10.6 | 39.6 | 49.8 |
| 80 nm | 1.1 | 37.4 | 61.5 |
| 120 nm | 0.1 | 36.8 | 63.1 |

What is claimed is:

1. A method for performing ultra fast thermal cycling of a fluidic sample, the method comprising:
   providing a micro-fluidic thermal cycling chamber defined by opposing first and second thin films;
   filling the micro-fluidic thermal cycling chamber with the fluidic sample;
   illuminating the first thin film with a light source;
   wherein a first portion of light illuminated onto the first thin film is absorbed into the first thin film and a second portion of the light illuminated onto the first thin film is transmitted through the first thin film;
   illuminating the second thin film with the light transmitted through the first thin film;
   wherein at least a portion of the transmitted light illuminating the second thin film is absorbed into the second thin film;
   uniformly elevating a temperature of the first thin film and a temperature of the second thin film as a function of the absorbed light into the first thin film and second thin film; and
   heating the fluidic sample within the micro-fluidic thermal cycling chamber as a result of the elevated temperature of the first thin film and second thin film.

2. The method of claim 1, wherein illumination of the first thin film is intermittently applied to perform ultra fast micro-fluidic polymerase chain reaction (PCR) of the fluidic sample.

3. The method of claim 2, wherein uniformly elevating the temperature of the first thin film and second thin film comprises:

illuminating the first and second thin films for a first duration to raise the temperature of the fluid sample in the micro-fluidic thermal cycling chamber to a selected temperature for a first period;

illuminating the first and second thin films for a second duration to raise the temperature of the fluid sample in the micro-fluidic thermal cycling chamber to a selected temperature for a second period;

illuminating the first and second thin films for a third duration to raise the temperature of the fluid sample in the micro-fluidic thermal cycling chamber to a selected temperature for a third period; and repeating a cycle of illumination periods for multiple cycles to amplify the fluid sample.

4. The method of claim 2, wherein the first thin film has a first thickness, and the second thin film has a second thickness different than the first thickness.

5. The method of claim 4, wherein the first thin film thickness and second thin film thickness are selected so as to match a rate of absorption of light into the first thin film and second thin film such that the first thin film and second thin film have a substantially uniform rate of temperature elevation.

6. The method of claim 2, further comprising:
measuring a temperature within the micro-fluidic thermal cycling chamber.

7. The method of claim 2, wherein the first thin film and second thin film have a surface covered with a passivation layer to prevent PCR reaction inhibition within the micro-fluidic thermal cycling chamber.

8. The method of claim 2, wherein filling the micro-fluidic thermal cycling chamber with the fluidic sample comprises:
injecting fluidic sample into the cycling chamber through a first port coupled to the micro-fluidic thermal cycling chamber;
wherein the injected fluid sample pushes air out of a second port coupled to the micro-fluidic thermal cycling chamber.

9. The method of claim 2, wherein the micro-fluidic thermal cycling chamber is configured for lasing of fluorescent emission during the PCR reaction.

* * * * *